(12) United States Patent
Striegler et al.

(10) Patent No.: US 8,296,858 B2
(45) Date of Patent: Oct. 23, 2012

(54) FLEXIBLY DISPLACEABLE COUPLING DEVICE FOR ACOUSTICALLY EXCITED ATOMIC FORCE MICROSCOPY WITH ACOUSTIC EXCITATION OF THE SAMPLE

(75) Inventors: André Striegler, Dresden, DE (US); Sascha Naumann, Dresden, DE (US)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 0 days.

(21) Appl. No.: 13/143,839

(22) PCT Filed: Feb. 2, 2010

(86) PCT No.: PCT/DE2010/000110
§ 371 (c)(1),
(2), (4) Date: Aug. 16, 2011

(87) PCT Pub. No.: WO2010/085948
PCT Pub. Date: Aug. 5, 2010

(65) Prior Publication Data
US 2011/0296563 A1    Dec. 1, 2011

(30) Foreign Application Priority Data
Feb. 2, 2009  (DE) .......................... 10 2009 008 251

(51) Int. Cl.
*G01N 13/16* (2006.01)
*G01N 29/00* (2006.01)
*G01N 29/06* (2006.01)
*G01Q 60/24* (2010.01)

(52) U.S. Cl. ................. 850/14; 850/33; 366/124; 367/7; 73/587; 73/644

(58) Field of Classification Search ................. 850/33, 850/14; 73/587, 644; 366/124; 367/7
See application file for complete search history.

(56) References Cited

U.S. PATENT DOCUMENTS
4,977,544 A * 12/1990 Karaki et al. ................. 367/7
(Continued)

FOREIGN PATENT DOCUMENTS
DE     3924006 A1    1/1990
(Continued)

OTHER PUBLICATIONS
International Search Report for corresponding PCT application PCT/DE2010/000110, dated May 7, 2010.
(Continued)

*Primary Examiner* — Nikita Wells
(74) *Attorney, Agent, or Firm* — Matthew B. Dernier, Esq.; Timothy X. Gibson

(57) ABSTRACT

A coupling device for an atomic force microscope with acoustic sample excitation includes a sound generator, in particular an ultrasonic test head, and designed for coupling of sound waves generated using the sound generator into a sample body for the acoustic excitation of the sample body, where the coupling device has a liquid reservoir fillable and/or filled with a liquid in its inner space; the lower side of the sample body can be arranged and/or is arranged laterally displaceably on the liquid reservoir; the end of the sound generator formed for coupling the sound waves into the sample body is arranged in the inner space of the liquid reservoir and/or that sound waves can be coupled into the inner space with this end; and the spatial section of the inner space of the liquid reservoir disposed between this end and the lower side of the sample body is completely fillable and/or filled with the liquid.

17 Claims, 3 Drawing Sheets

U.S. PATENT DOCUMENTS

| | | | |
|---|---|---|---|
| 4,977,779 A | 12/1990 | Karaki | |
| 5,675,075 A * | 10/1997 | Arnold et al. | 73/105 |
| 6,967,764 B2 * | 11/2005 | Birk | 359/305 |
| 7,360,404 B2 | 4/2008 | Reinstadtler | |
| 7,942,568 B1 * | 5/2011 | Branch et al. | 366/127 |
| 2006/0075807 A1 | 4/2006 | Elrod | |
| 2006/0150719 A1 | 7/2006 | Reinstadtler | |
| 2008/0276695 A1 | 11/2008 | Prater | |

FOREIGN PATENT DOCUMENTS

| | | |
|---|---|---|
| DE | 10237627 A1 | 3/2004 |

OTHER PUBLICATIONS

International Preliminary Report and Written Opinion for corresponding PCT application PCT/DE2010/000110, dated Aug. 2, 2011.

* cited by examiner

FLEXIBLY DISPLACEABLE COUPLING DEVICE FOR ACOUSTICALLY EXCITED ATOMIC FORCE MICROSCOPY WITH ACOUSTIC EXCITATION OF THE SAMPLE

BACKGROUND

The present invention relates to a coupling device for an atomic force microscope with acoustic sample excitation in accordance with the preamble of claim 1, to a corresponding atomic force microscope and to a corresponding method for sound coupling at such an atomic force microscope with acoustic sample excitation. The coupling device in accordance with the invention can in this respect in particular be used within the framework of the so-called AFAM technique (AFAM=atomic force acoustic microscopy) as well as for other apparatus and methods based on atomic force microscopy in which the acoustic excitation takes place via the sample. The present invention can in particular also be used in the UFM technique (UFM=ultrasonic force microscopy). The invention will be explained in the following with reference to the AFAM technique, a significant representative of atomic force microscopy with acoustic sample excitation.

The AFAM technique is already familiar to the skilled person (U.S. Pat. No. 5,675,075). This technique is used for the high-resolution imaging of qualitative, elastic differences or for the quantitative measurement of elastic properties of sample bodies or of samples. In this technique, a sample is acoustically coupled to an ultrasonic generator (ultrasonic test head). In this respect, the sample body is located on the sound generator, with a thin film of a coupling means (e.g. viscous glycerin, hardened silver conductive lacquer, or similar) being located between the sample and the test head. This structure makes it possible to couple longitudinal sound waves into the sample and to excite the sample surface to continuous vertical oscillations (so-called out-of-plane oscillations). These oscillations are then coupled via the sensor tip lying over it into the AFM spring hanger of the atomic force microscope. The resonance behavior of the resulting spring hanger oscillations is evaluated (e.g. position of the contact resonance frequencies) to determine elastic properties of the sample. FIG. 1 shows for this purpose the principle of the AFAM technique known from the prior art (B is the plate spring or the cantilever with the needle fastened thereto for the scanning of the sample).

In the above-described apparatus and methods as with the other apparatus and methods known from the prior art, the sample is fixedly fixed to the ultrasonic generator or the ultrasonic test head by a viscous or hardened acoustic coupling means. A substantial disadvantage thereby results such that the sample and the sound generator are not mutually laterally displaceable. The acoustic excitation of surface oscillations is therefore very locally restricted. Measurement sites on samples having a large surface such as silicon wafers or photomasks can therefore only be examined with an increased time effort (due to the required releasing and refastening of the ultrasonic test head) and/or material effort (use of a plurality of ultrasonic heads).

A further disadvantage of the methods of the prior art is that the residue-free removal of the coupling means after the measurement requires a substantial effort. The use of typical coupling means such as glycerin or silver conductive lacquer is only possible with great limitations under clean room conditions and under the assumption of a desired further use of the sample.

SUMMARY OF THE INVENTION

Starting from the prior art, it is therefore the object to further develop the known coupling devices such that in particular also large-area samples can be measured using atomic force microscopy by means of acoustic excitation of the sample with a small time effort. It is furthermore the object to further develop the known coupling devices such that the measured samples can be further used without restriction. It is finally the object of the present invention to provide corresponding methods for sound coupling.

This object is achieved by a coupling device in accordance with the features disclosed and described herein, including an atomic force microscope, a method for sound coupling, and other combinations.

The present invention will be described in the following, first generally and then with reference to two embodiments. A plurality of individual features or elements of the present invention which are described in combination with one another in the following description in this respect do not have to exist in the shown combination with one another, but can also be implemented independently of one another within the framework of the present invention which is defined by the attached claims. Individual ones of the shown features can thus in particular also be realized within the framework of the invention without also having to realize the other individual features described in the respective combination.

The flexibly displaceable coupling of sound generators (in particular: ultrasonic test heads) for atomic force microscopes implemented in accordance with the invention in which an acoustic excitation of the sample takes place will be described in the following.

A coupling device in accordance with the invention first includes a sound generator (in particular: ultrasonic test head) which is designed for coupling the sound waves generated with it into the sample. The coupling device furthermore has a liquid reservoir which is filled in its inner space with a liquid (in particular: water) used for acoustic coupling. This liquid reservoir is designed so that the sample to be measured can be laterally displaceably supported and/or arranged on it or above it. The end of the sound generator designed for coupling the sound waves into the sample body is then arranged in the inner space of the liquid reservoir, with the liquid reservoir and this end being arranged and aligned such that the space section of the inner space of the liquid reservoir disposed between this end and the sample body is completely filled with the acoustic coupling liquid. A deterioration of the coupling of the sound waves from the coupling end of the sound generator into the sample body is prevented by the corresponding complete filling of this space section.

Alternatively to the arrangement of the above-described end of the sound generator in the inner space of the liquid reservoir, the sound generator can, however, also be arranged outside (e.g. beneath) the liquid reservoir and be connected to the liquid reservoir (e.g. with the aid of a membrane) so that the sound waves can be coupled into the inner space of the liquid reservoir and thereupon into the sample body using the said end of the sound generator.

The liquid reservoir is particularly preferably formed (e.g. by suitable formation of the upper rim of the liquid reservoir) such that a liquid film can be formed between it and the lower side of the sample body.

In a further advantageous embodiment, the liquid reservoir is an upwardly open and horizontally terminated liquid reservoir on whose upper rim or above the upper rim the sample body can then be arranged and/or supported (aligned horizontally). The upper rim of the reservoir can then be designed so that a thin liquid film is formed between it and the lower side of the sample body. This is in particular possible in that the upper rim of the liquid reservoir (which can be formed in the form of a trough or similar) has a widened portion viewed in the horizontal plane. Such a widened portion can, for example, be a flat, ring-shaped element which is placed onto the upper edge of a cylindrical liquid container having the same diameter and be sealingly connected to this upper edge. The sample body can then be displaceably placed onto the ring-shaped element from above so that said thin liquid film arises between its lower side and the upwardly disposed surface of the ring-shaped element.

The advantageous formation of the liquid film between the surface upwardly terminating the liquid container and the lower side of a sample body can in particular be implemented in that a bearing unit is provided which extends slightly beyond the liquid reservoir (in particular its upper edge or its upper rim) in the direction of the vertical and seen from bottom to top so that this vertical difference between the upper termination of the bearing unit and the liquid reservoir corresponds to the desired liquid film thickness. The sample body is then placed onto this bearing unit in a planar fashion. Such a bearing unit can in the simplest case be a bearing unit which comprises three or four vertically aligned elements (legs) which are of equal length, are of columnar form and onto which the sample body can then be fastened and/or placed. The sound generator and liquid reservoir can then be arranged at the center or between the individual elements of the bearing unit such that a lateral (horizontal) displacement of the sound generator together with the liquid reservoir is possible relative to the sample body and to the bearing unit.

The above-described spatial embodiment of the individual elements is particularly preferable so that a liquid film having a thickness between 20 and 1000 µm, particularly preferably between 100 and 500 µm, results.

As described in more detail in the following in the embodiments, the liquid reservoir can be a reservoir that only sealingly surrounds the (upwardly disposed) end of the sound generator designed for sound coupling (formation of the liquid reservoir as a peripheral, liquid-filled trench).

It is, however, alternatively also possible to form the liquid reservoir as a tank whose height is larger than that of the total sound generator so that the sound generator can be completely introduced into such an upwardly open tank (the intermediate spaces between the inner wall of this housing and the outer wall of the sound generator and the region between the upper edge of the sound generator and the upper termination of the housing is then filled with the liquid).

To ensure a constant acoustic excitation of the sample body, the liquid reservoir can be connected via a hose to a compensation container filled with the liquid. A regulation apparatus can then be provided at the compensation container so that the liquid level and the pressure in the inner space region of the liquid reservoir is held constant (this also e.g. prevents an air bubble formation in the intermediate space region between the end of the sound generator formed for coupling in the sound waves and the surface section of the sample body provided for coupling in the sound waves). Alternatively to this, the compensation container can also be designed and arranged simply (e.g. by an arrangement of the container at a suitable level above the liquid reservoir) so that a sufficient pressure can be ensured in the inner space of the liquid reservoir solely by this arrangement and design (i.e. without a regulation apparatus).

In particular water, preferably ultrapure water, can be used as the coupling liquid.

In principle, any water can be used. It should, however, at least be lime-free to avoid lime deposits by water evaporation. In particular the use of higher quality water is required for the use under clean room conditions.

The present invention thus avoids the previous fixed connection between the sound generator and the sample body and the disadvantages associated therewith. A large-area sample is now laterally displaceable as desired with a fixed sound generator or ultrasonic test head (alternatively to this, the ultrasonic test head can also be displaced beneath the sample with a fixed sample). Both parts (coupling unit or its upper rim and/or liquid reservoir, on the one hand, and sample body, on the other hand) are advantageously only still connected by low adhesion forces of a thin water film (for example, 100 to 500 µm thick). On the use of ultrapure water as the acoustic coupling means, no residues remain at the sample after the drying. A previously required time-consuming purifying of the sample is hereby dispensed with. A use of the acoustic excitation under clean room conditions is thus possible.

The main advantage of the present invention thus comprises the possibility of any desired lateral displacement of a large-area sample without any change of the acoustic coupling. A further advantage, in particular by use of ultrapure water as a coupling liquid, is the omission of a purifying step after the examination of the sample. It was previously necessary to remove the acoustic coupling means used, such as glycerin or silver conductive lacquer, in a time-consuming manner. A use of a measuring system of atomic force microscopy with acoustic excitation of the sample under clean room conditions is thus possible.

The present invention can in particular be used with atomic force microscopy with acoustic excitation of the sample (e.g. AFAM technique) at very large-area samples or at a plurality of small samples which are acoustically coupled on a carrier plate. Examples for very large-area samples (on which then a large number of measurement points should be measured) are silicon wafers or photomasks. These samples can be measured with a substantial reduction of the measuring times. The rear side or lower side of the samples to be examined then has to be planar as a rule.

BRIEF DESCRIPTION OF THE DRAWINGS

The present invention will be described in the following with reference to two embodiments. There are shown for this purpose.

DETAILED DESCRIPTION OF THE INVENTION

Figure 2:
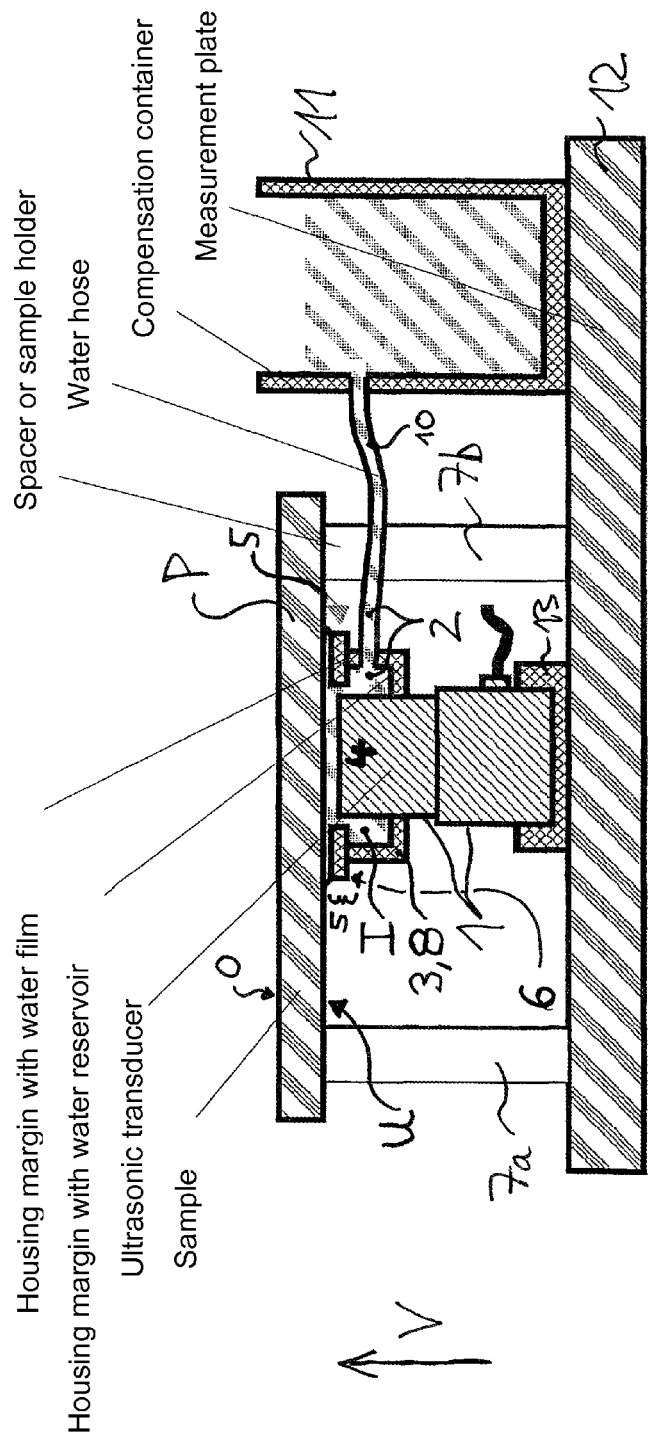
FIG. 2 shows a first coupling device in accordance with the invention for an atomic force microscope with acoustic sample excitation.

FIG. 2 shows in a side view in the horizontal plane perpendicular to the vertical V of a cross-section through a first coupling device in accordance with the invention for an atomic force microscope (the components of the atomic force microscope itself are not shown here for reasons of clarity; the sample shown is scanned at its upper side O by the cantilever of the microscope).

A holder 13 for the ultrasound test head 1 is fixed on a horizontally arranged measuring plate 12 of the system. The ultrasound test head 1 is likewise fixed in the holder 13 so that it is not movable relative to the holder 13 and the plate 12. The ultrasound test head 1 here comprises two cylindrical elements arranged above one another, with the upwardly disposed cover area region of the upper cylinder being formed as an end 4 of the sound generator 1 for coupling sound waves into the sample body P.

In the region of this upwardly disposed end 4 of the sound generator 1, the sound generator 1 is radially symmetrically surrounded by a ring-shaped spacer ring 3 which (together with the element 5 described in the following). The spacer ring which is L-shaped in cross-section is in this respect sealingly arranged at the outer periphery of the upper end 4 of the sound generator so that an intermediate space having a constant extent over the periphery of the sound generator results between the outer cylinder wall of the upper end 4 and the vertically arranged wall section of the liquid reservoir ring element 3. This intermediate space, also called an inner space 1 in the following, then serves as an interior of the liquid reservoir 3 which is filled with a liquid 2 (here: ultrapure water). The horizontally arranged base section of the L-shaped ring element is sealingly connected to the vertical outer wall (cylinder jacket surface) of the upper end 4 of the sound generator 1.

The L-shaped ring section 3 has a flat, ring-shaped element 5 at its upwardly terminating end which is arranged in the horizontal and is sealingly connected to the L-shaped ring element of the liquid reservoir 3. The horizontal ring element 5 which is placed on centrally (viewed with respect to the end 4 and the L-shaped section) in this respect projects upwardly in the vertical direction V slightly beyond the upper edge of the end 4 so that a liquid-filled spatial region results above the end 4 on the complete filling of the inner space I of the liquid reservoir 3 with liquid 2.

The upwardly disposed flat ring section 5 of the liquid reservoir 3 is in the present case thus formed as a widened section 6 (viewed in the horizontal plane) of the vertical outer wall of the liquid reservoir 3. In the present case, the liquid reservoir 3 is thus a housing section 8 sealingly connected to the end 4 of the sound generator 1 and extending about this end 4.

The coupling device has a bearing unit 7 on a concentric circle about the arrangement of the elements 1 to 8 and spaced apart from this arrangement. Said bearing unit here comprises three individual columnar bearing elements 7a to 7c (only the two elements 7a and 7b are visible) which are aligned in the vertical direction V, which are of equal length and which are set on the plate 12. The upper ends of the columnar elements 7 are formed as surfaces disposed in the horizontal. Viewed in the vertical V, these upper end surfaces of the column legs 7 are disposed slightly above the upwardly disposed surface of the flat ring element 5 so that, when the sample body P is placed onto the legs 7 and when it is aligned in the horizontal between the lower side U of the sample body P and the upwardly disposed surface of the flat ring section 5, a small intermediate space having a height in the range between 100 μm and 500 μm results (spacing of the lower side U of the sample body P from the upper rim of the liquid reservoir 3). This slight intermediate space can be set with respect to its height in the vertical direction V precisely to a desired water film thickness by a vertical adjustment of the column legs 7 (not shown). The reservoir 3 (or ring element 5) and the lower side U of the sample P are then only still connected by small adhesion forces of a thin water film formed between these elements so that the sample can be laterally easily displaced with a fixed test head 1 (for example, by a suitably designed lateral displacement mechanism for the column legs 7 with a sample P, not shown here, fixedly arranged thereon). In this manner, the sample P can be scanned over a large area by a lateral movement of the sample P while keeping the acoustic excitation conditions constant. Alternatively to this, it is, however, also possible to arrange the column legs 7 and the sample P arranged thereon fixedly on the measurement plate 12 and to form the holder 13, together with the elements 1 to 8 arranged thereon, laterally displaceably.

To keep the acoustic excitation conditions (or the pressure), the liquid level in the inner space region I of the liquid reservoir 3 and the liquid film between the lower side U of the sample and the upper side of the ring element 5 constant, the inner space I of the liquid reservoir 3 is connected via a hose 10 to a compensation container 11 which is likewise filled with the liquid 2. This compensation container 11 is provided with a regulation apparatus (not shown) with which a keeping constant of the pressure and a constant liquid level in the liquid reservoir 3 or inner space I can be effected.

On a lateral movement of the sample P, the ultrasonic test head 1 is fixed precisely beneath the sensor tip of the atomic force microscope (not shown). An adapter 3 in whose inner space the coupling liquid 2 is located is thus fastened in the upper region of the test head 1. Since there may be a risk of air bubble formation by evaporation of coupling liquid 2, evaporated water is replaced with a thin hose 10 from the compensation container 11. A constant pressure is implemented in the reservoir and thus a constant acoustic excitation over a time period of almost any desired length, also on a lateral movement, by the previously described filling level regulation in the container 11.

The sound field above the ultrasonic test head 1 (that is between the lower side U of the sample P and the upper end 4 of the test head 1) thus does not change when the sample P is displaced in the lateral direction. The sample P, which is smooth on the rear side, is here guided in a plano-parallel manner to the measurement plate 12 of the measuring system (for example, granite table of an AFM atomic force microscope).

Figure 1:
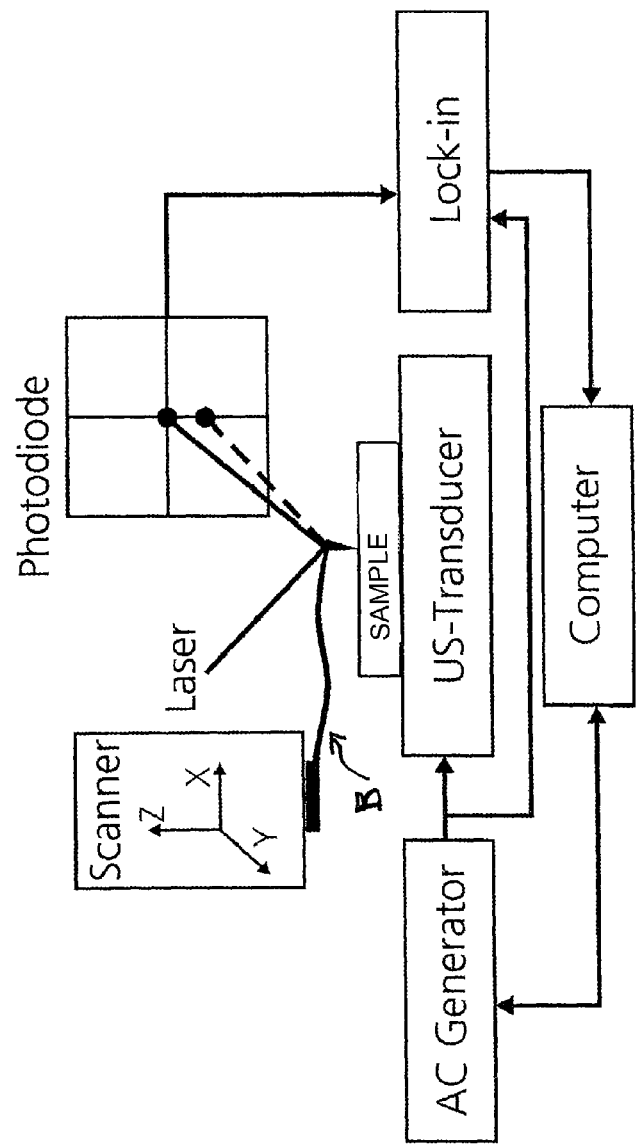
FIG. 1 shows for this purpose the principle of the AFAM technique known from the prior art (B is the plate spring or the cantilever with the needle fastened thereto for the scanning of the sample).

The guidance can be implemented conventionally via manual or powered displacement. The sample should as a rule only be displaced in the x-y plane with respect to the fixed coupling device. The given plano-parallelism of the lower sample side to the housing margin as well as to the active test head surface ensures a constant peripheral water film thickness between the housing rim and the lower sample side on the sample displacement. A planar measurement plate is as a rule only required with the manual guidance (see FIGS. 1 and 2).

To avoid air bubble formation in the interior of the water reservoir with a moving sample P, the upper margin 5 of the adapter is made widened 6.

Due to parallel boundary surfaces in the sound field above the test head 1, a resonance behavior of the surface oscillation can occur with the given measuring arrangement. Said resonance behavior is caused on the coupling in of longitudinal sound waves by vertical waves in the water layer and in the sample body. Such resonance magnifications are of a very narrow band and can easily be displaced into non-critical frequency ranges outside the measuring frequencies by variation of the water film thickness (that is of the thickness between the upper edge of the end 4 and of the lower side U) and/or of the sample thickness. A variation of the sample thickness is, for example, easily possible by coupling additional flat intermediate bodies. Such an intermediate body is used in such a case as the body P shown in FIG. 2 and the sample body actually to be measured is then arranged on this intermediate body.

With large-area thin sample bodies (e.g. silicon wafers having a diameter of 300 mm), the use of a thicker intermediate body (e.g. a glass plate as the body P) is equally required for the avoidance of any deflection of the body actually to be measured. With thin samples (e.g. silicon wafers having a diameter of 300 mm with a thickness of only 500 μm), the sample body P is thus optionally in two parts. The actual sample is arranged vertically above and a so-called thicker additional intermediate body vertically below (not shown in FIGS. 2 and 3). Both parts have to be acoustically coupled, for example by water. Furthermore, a plurality of small samples can be arranged on the above-named intermediate body by means of a suitable acoustic coupling.

The coupling can advantageously be implemented using ultrapure water in each of these cases.

A head of the type Parametrics V 106-RM of the company Olympus NDT having a center frequency of 2.25 MHz can be used as the ultrasonic test head 1. Such a test head has an advantageous geometry with an outer diameter of approximately 18 mm, a diameter of the active surface of 15 mm (upper side of the end 4) and a height (in the vertical direction V) of approximately 16 mm. Such sonic heads with comparatively compact dimensions are frequently in particular used with AFAM measurements. The width of the housing rim 5 (ring width in the horizontal direction) for the realization of the thin water film can be reduced to 5 mm, for example.

A prototype described in this embodiment has been used successfully during long AFAM examinations at photomasks. The corresponding measuring times were able to be considerably reduced in comparison with the prior art.

The measuring time is reduced by at least the factor 2 since the ultrasonic test head does not have to be cleaned before every single measurement and the ultrasonic test head has to be coupled fixedly locally. The last step is as a rule very time consuming.

Figure 3:
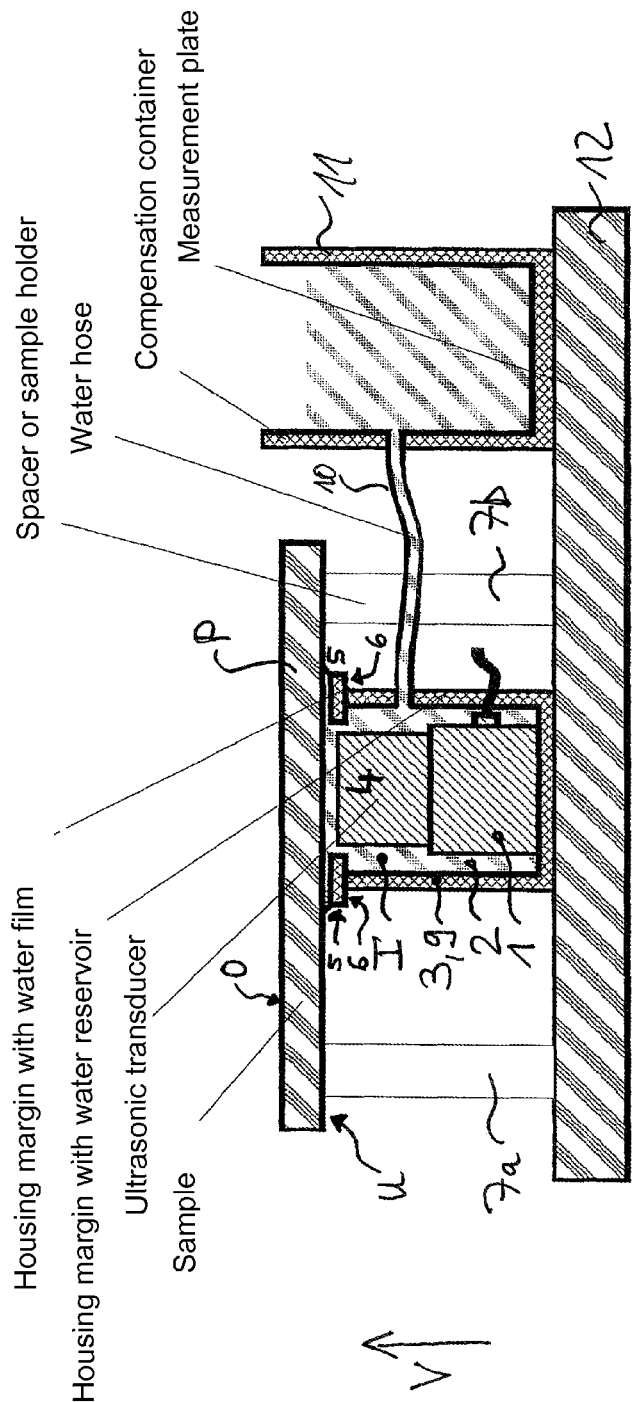
FIG. 3 shows a second coupling device in accordance with the invention.

FIG. 3 shows a further variant of the present invention. This variant is generally structured like the coupling device shown in FIG. 2 so that only the differences will be described in the following. The variant shown in FIG. 3 is in particular advantageous with limited space relationships at the housing margin: In this variant, the ultrasonic test head 1 stands completely in a liquid reservoir 3 formed as a water container 9. The housing body 9 formed as a hollow cylinder open at one side (upwardly) thus completely takes up or surrounds the sound generator 1 immersed in the liquid 2. The lower side of the housing body then serves the fastening on the plate 12 so that the element 13 is omitted here.

An automatic filling level regulation for the compensation container 11 for the compensation of water evaporation is then also easily possible in this variant.

The coupling device in accordance with the invention can also be used in ultrasonic technology in which sound is conveyed into a test body and a reflected or transmitted signal is received and evaluated. The coupling device can here be used in special applications, wherein the total sample cannot or may not be wetted with the coupling means (immersion technique).

The invention claimed is:

1. A coupling device for an atomic force microscope with acoustic sample excitation comprising a sound generator, in particular an ultrasonic test head, and designed for coupling of sound waves generated using the sound generator into a sample body for acoustic excitation of the sample body,
    wherein the coupling device has a liquid reservoir fillable and/or filled with a liquid in its inner space;
    wherein a lower side of the sample body can be arranged and/or is arranged laterally displaceably on the liquid reservoir and/or thereabove;
    wherein an end of the sound generator formed for coupling the sound waves into the sample body is arranged in the inner space of the liquid reservoir and/or wherein sound waves can be coupled into the inner space with this end; and
    wherein the spatial section of the inner space of the liquid reservoir disposed between this end and the lower side of the sample body is completely fillable and/or filled with the liquid.

2. A coupling apparatus in accordance with claim 1, wherein the liquid reservoir, in particular an upper rim of the liquid reservoir, is designed so that a liquid film can be formed and/or is formed between it and the lower side of the sample body.

3. A coupling device in accordance with claim 2, further comprising an upwardly open and horizontally terminating liquid reservoir on which, in particular on its upper rim, and/or above which, in particular above its upper rim, the lower side of the sample body can be arranged and/or is arranged horizontally.

4. A coupling device in accordance with claim 2, wherein the liquid reservoir is upwardly terminated, in particular by means of its upper rim, by a horizontally arranged, planar surface section; and/or the liquid reservoir, in particular its upper end and/or its upper rim, has a widened portion and/or a planar platform, in particular a ring-shaped platform.

5. A coupling device in accordance with claim 1, further comprising a bearing unit comprising at least three vertically aligned, columnar elements, and/or an x/y displacement table on which bearing unit the sample body can be placed and/or is placed in the horizontal and/or with which bearing unit the sample body is displaceable in the horizontal and whose upper end projects in the vertical beyond the liquid reservoir, in particular its upper rim, so that a liquid film can be formed and/or is formed between the liquid reservoir, in particular its rim, and the lower side of the sample body.

6. A coupling device in accordance with claim 2, wherein the liquid film can be formed and/or is formed with a thickness of one of: (i) between 20 μm and 1000 μm, (ii) between 100 μm and 500 μm, and (iii) including limit values.

7. A coupling device in accordance with claim 1, further comprising a housing section as a liquid reservoir sealingly connected to the end of the sound generator formed for coupling the sound waves into the sample body and extending about this end viewed in the horizontal, with the housing section preferably being formed as ring-shaped, elliptical or rectangular and/or so that the coupling of oscillations generated by the sound generator into the sample body is not impeded by the housing section.

8. A coupling device in accordance with claim 7, wherein the housing section is designed as a ring section which is fillable and/or filled with the liquid and extends concentrically about the end of the sound generator which is cylinder-shaped and arranged with is upper cylinder cover surface in the horizontal.

9. A coupling device in accordance with claim 1, further comprising a housing as a liquid reservoir completely receiving and sealingly terminating the sound generator.

10. A coupling device in accordance with claim 9, wherein the housing has a wall section which is preferably arranged perpendicular to the horizontal and which runs concentrically about the sound generator formed radially symmetrically about a vertical axis.

11. A coupling device in accordance with claim 1, further comprising a compensation container connected to the inner space of the liquid reservoir for liquid exchange, via a hose, and fillable and/or filled with the liquid.

12. A coupling device in accordance with claim 11, wherein the compensation container is designed and/or arranged so that and/or a regulation apparatus, in particular a regulation apparatus for the liquid filling level in the compensation container, is provided so that the liquid level and/or the pressure in the inner space region of the liquid reservoir can be kept constant by means of the compensation container.

13. A coupling device in accordance with claim 1, wherein the liquid contains or comprises water, in particular ultrapure water.

14. An atomic force microscope comprising:
a coupling device comprising a sound generator, in particular an ultrasonic test head, and designed for coupling of sound waves generated using the sound generator into a sample body for acoustic excitation of the sample body,
wherein the coupling device has a liquid reservoir fillable and/or filled with a liquid in its inner space;
wherein a lower side of the sample body can be arranged and/or is arranged laterally displaceably on the liquid reservoir and/or thereabove;
wherein an end of the sound generator formed for coupling the sound waves into the sample body is arranged in the inner space of the liquid reservoir and/or wherein sound waves can be coupled into the inner space with this end; and
wherein the spatial section of the inner space of the liquid reservoir disposed between this end and the lower side of the sample body is completely fillable and/or filled with the liquid.

15. A method for coupling sound to an atomic force microscope with acoustic sample excitation,
wherein sound waves are coupled into a sample body for its acoustic excitation using a sound generator, including an ultrasonic test head, which is designed for coupling generated sound waves into the sample body;
wherein a liquid reservoir is filled with a liquid in its inner space;
wherein a lower side of the sample body is arranged laterally displaceably on the liquid reservoir or thereabove;
wherein an end of the sound generator formed for coupling the sound waves into the sample body is arranged in the inner space of the liquid reservoir and/or wherein sound waves are coupled into the inner space with this end; and
wherein a spatial section of the inner space of the liquid reservoir disposed between this end and a lower side of the sample body is completely filled with the liquid.

16. A method in accordance with claim 15, wherein the sound is generated and coupled using a coupling device,
wherein the coupling device includes a sound generator, in particular an ultrasonic test head, and designed for coupling of sound waves generated using the sound generator into a sample body for acoustic excitation of the sample body,
wherein the coupling device has a liquid reservoir fillable and/or filled with a liquid in its inner space;
wherein a lower side of the sample body can be arranged and/or is arranged laterally displaceably on the liquid reservoir and/or thereabove;
wherein an end of the sound generator formed for coupling the sound waves into the sample body is arranged in the inner space of the liquid reservoir and/or wherein sound waves can be coupled into the inner space with this end; and
wherein the spatial section of the inner space of the liquid reservoir disposed between this end and the lower side of the sample body is completely fillable and/or filled with the liquid.

17. A method, comprising:
acoustically exciting atomic force microscopy at larger-area and/or flat sample bodies, at semiconductor wafers or photomasks, and/or at a plurality of preferably small sample bodies which are fixed on a preferably large-area intermediate body, using a coupling device,
wherein the coupling device includes a sound generator, in particular an ultrasonic test head, and designed for coupling of sound waves generated using the sound generator into a sample body for acoustic excitation of the sample body,
wherein the coupling device has a liquid reservoir fillable and/or filled with a liquid in its inner space;
wherein a lower side of the sample body can be arranged and/or is arranged laterally displaceably on the liquid reservoir and/or thereabove;
wherein an end of the sound generator formed for coupling the sound waves into the sample body is arranged in the inner space of the liquid reservoir and/or wherein sound waves can be coupled into the inner space with this end; and
wherein the spatial section of the inner space of the liquid reservoir disposed between this end and the lower side of the sample body is completely fillable and/or filled with the liquid.

* * * * *